US008734827B2

(12) United States Patent
Chan et al.

(10) Patent No.: US 8,734,827 B2
(45) Date of Patent: May 27, 2014

(54) BIOENGINEERED INTERVERTEBRAL DISCS AND METHODS FOR THEIR PREPARATION

(75) Inventors: Barbara Pui Chan, Ap Lei Chau (HK); Kenneth Man-Chee Cheung, Mid-Levels (HK); Danny Chan, Ap Lei Chau (HK); Godfrey Chi-Fung Chan, Causeway Bay (HK); Ting Yan Hui, Ma on Shan (HK)

(73) Assignee: University of Hong Kong, Hong Kong (HK)

( * ) Notice: Subject to any disclaimer, the term of this patent is extended or adjusted under 35 U.S.C. 154(b) by 1183 days.

(21) Appl. No.: 11/742,040

(22) Filed: Apr. 30, 2007

(65) Prior Publication Data

US 2007/0292514 A1 Dec. 20, 2007

Related U.S. Application Data

(60) Provisional application No. 60/796,088, filed on Apr. 28, 2006.

(51) Int. Cl.
*A61F 2/44* (2006.01)
*C12N 5/0775* (2010.01)
*A61F 2/28* (2006.01)
*A61K 38/39* (2006.01)

(52) U.S. Cl.
USPC .......... 424/423; 424/422; 424/93.7; 435/366; 435/401

(58) Field of Classification Search
CPC ........... A61F 2/442; A61F 2/02; A61F 2/466; A61F 2002/307; C12N 5/0012; C12N 5/0068; C12N 5/0697; C12N 2533/54
See application file for complete search history.

(56) References Cited

U.S. PATENT DOCUMENTS

| | | | |
|---|---|---|---|
| 5,964,807 A | 10/1999 | Gan et al. | |
| 6,240,926 B1 | 6/2001 | Chin-Gan et al. | |
| 6,541,024 B1 | 4/2003 | Kadiyala et al. | |
| 6,723,335 B1 | 4/2004 | Moehlenbruck et al. | |
| 6,783,546 B2 | 8/2004 | Zucherman et al. | |
| 2006/0159665 A1* | 7/2006 | Giannetti | 424/93.7 |
| 2007/0003525 A1* | 1/2007 | Moehlenbruck et al. | 424/93.7 |
| 2007/0098675 A1* | 5/2007 | Elisseeff et al. | 424/78.3 |
| 2008/0038233 A1* | 2/2008 | Freemont et al. | 424/93.21 |
| 2009/0142311 A1* | 6/2009 | Masuda et al. | 424/93.7 |

OTHER PUBLICATIONS

Bergeret-Galley, et al., "The value of a new filler material in corrective and cosmetic surgery: DermaLive and DermaDeep", *Aesthetic Plast Surg.*, 25(4):249-55 (2001).
Brisby, et al., "Cell therapy for disc degeneration—potentials and pitfalls", *Orthop. Clin. North Am.*, 35(1):85-93 (2004).
Corcos, et al., "Multicenter randomized clinical trial comparing surgery and collagen injections for treatment of female stress urinary incontinence", *Urology*, 65(5):898-904 (2005).
Elliott and Sarver, "Young investigator award winner: validation of the mouse and rat disc as mechanical models of the human lumbar disc", *Spine*, 29(7):713-22 (2004).
Enker, et al., "Artificial disc replacement. Preliminary report with a 3-year minimum follow-up", *Spine*, 18(8):1061-70 (1993).
Griffith, et al., "A multicenter retrospective study of the clinical results of the LINK SB Charite intervertebral prosthesis. The initial European experience", *Spine*, 19(16):1842-9 (1994).
Masuda, at al., "Growth factors and treatment of intervertebral disc degeneration", *Spine*, 29(23):2757-69 (2004).
Mizuno, at al., "Tissue-engineered composites of anulus fibrosus and nucleus pulposus for intervertebral disc replacement", *Spine*, 29(12):1290-7 (2004).
Rose, at al., "In vitro assessment of cell penetration into porous hydroxyapatite scaffolds with a central aligned channel", *Biomaterials*, 25(24):5507-14 (2004).
Sato, et al., "An atelocollagen honeycomb-shaped scaffold with a membrane seal (ACHMS-scaffold) for the culture of annulus fibrosus cells from an intervertebral disc", *J. Biomed. Mater. Res. A.*, 64(2):248-56 (2003).
Sato, at al., "Tissue engineering of the intervertebral disc with cultured annulus fibrosus cells using atelocollagen honeycombshaped scaffold with a membrane seal (ACHMS scaffold)", *Med. Biol. Eng. Comput.*, 41(3):365-71 (2003).
Seguin, et al., "Tissue engineered nucleus pulposus tissue formed on a porous calcium polyphosphate substrate", *Spine*, 29(12):1299-306 (2004).
Urban, et al., "Nutrition of the intervertebral disc", *Spine*, 29(23):2700-9 (2004).
Wallach, et al., "Gene therapy applications for intervertebral disc degeneration", *Spine*, 28(15 Suppl):S93-8 (2003).
Walsh, et al., "In vivo growth factor treatment of degenerated intervertebral discs", *Spine*, 29(2):156-63 (2004).

* cited by examiner

*Primary Examiner* — Maria Marvich
(74) *Attorney, Agent, or Firm* — Pabst Patent Group LLP

(57) ABSTRACT

A bioengineered IVD for disc replacement has been developed that has mechanical and structural support characteristics similar to those of native IVD. Extracellular matrix (ECM) provides support to living cell components and interacts with the living cellular components during the fabrication process without introducing toxicity. The composition can be produced from both natural or synthetic source but preferably natural and induced to self-assemble or reconstitute into its solid form under conditions that are mild enough to support cellular survival and growth. The cells induce a volume change of the structures, leading to changes in dimension, ECM density, cell density, mechanical property and stability, etc. The extent of the change in volume of the composition can be precisely controlled by factors such as the density of the ECM, the density of the living cells, the timing for interaction and the serum concentration. Increased structural support is provided by crosslinking.

21 Claims, 6 Drawing Sheets

BIOENGINEERED INTERVERTEBRAL DISCS AND METHODS FOR THEIR PREPARATION

CROSS-REFERENCE TO RELATED APPLICATIONS

This application claims priority to U.S. Ser. No. 60/796,088 filed Apr. 28, 2006.

FIELD OF INVENTION

The present invention relates generally to bioengineered intervertebral discs. More specifically, it relates to methods and compositions of producing intervertebral disc-like structures with living cells and natural extracellular matrix, and with mechanical properties comparable to native discs, for replacing degenerated discs in particular severe cases, and to the resulting bioengineered intervertebral discs.

BACKGROUND OF THE INVENTION

The intervertebral disc (IVD) separates the vertebrae of the spine and functions to resist loading that the spine is subjected to during daily life. It has a unique structure with an inner water-rich gel-like nucleus pulposus (NP) with random organization of extracellular matrix (ECM); an outer fibrous annulus fibrosis (AF) with well-organized collagen sheets; and thin cartilaginous end-plates supplying nutrients to the disc. Normal disc function is enabled by the special configuration and differential hydration properties of NP and AF. The NP is predominately in proteoglycans, which is hydrophilic, and therefore maintains a more than 80% hydration, providing high hydrostatic pressure to resist loading. The AF also contains more than 60% water and is predominately in closely-packed collagen providing strong tensile strength and assisting the NP in resisting loading. Disc cells are chondrocyte-like cells able to produce ECM in particular proteoglycans so as to maintain the hydration properties of IVD.

Disc degeneration is a common clinical problem affecting human populations worldwide, causing low back pain and limited mobility. Although the pathogenesis is not completely known, structural and compositional changes of degenerated discs are extensively characterized. In early disc degeneration, disc cells, in particular the NP cells, become less capable of synthesizing ECM, the gelatinous NP becomes more fibrous and therefore reduces the water content of the disc. As the disease progresses, there is more ECM and structural changes such as proteoglycan and collagen degradation, reducing disc height. At advanced stages, structural collapse and eventual loss of disc function in resisting loading result.

There is no satisfactory clinical treatment for advanced disc degeneration. Spinal fusion does not solve the problem but does relieve pain. However, the fused spine loses motility and is non-functional. The only clinically available option for replacement are artificial discs made of metal and rubber whose purpose is to preserve the motion between the vertebrae. However, these prostheses cannot integrate with the surrounding tissues and allow new tissue formation. Prosthetic failure and high re-operation rate has been reported (Enker, et al. Spine, 18(8):1061-70 (1993), Griffith, et al., Spine, 19(16):1842-9 (1994)).

Research and development efforts to restore disc function have been extensive, ranging from administration of growth factors, for example, multiple injections of transforming growth factor-beta (TGF-b), insulin-like growth factor-1 (IGF-1), and basic fibroblast growth factor (bFGF), to stimulate disc cell secretion of ECM (Walsh, et al., Spine, 29(2): 156-63 (2004)); gene therapy to deliver cDNA coding for several growth factors stimulating ECM synthesis (Wallach, et al. Spine, 28(15 Suppl):S93-8 (2003)) and cell therapy where mature autologous disc cells, chondrocytes, or stem cells are transplanted to the intervertebral disc to replenish the cells and enhance ECM production (Brisby, et al., Orthop. Clin. North Am., 35(1):85-93 (2004)). These methods are for early stage degeneration where the disc is still functional and retains its structural integrity, not in advanced degenerative cases, where structural and functional replacement is needed.

One approach to treating advanced disc degeneration is to replace a non-functional disc with a tissue engineered substitute resuming the disc function immediately after implantation, integrating with the surrounding tissues and maintaining its function. In general, the substitute consists of a scaffold, which provides structural and functional support with good stability for a substantial amount of time to allow new tissue growth; cellular components embedded in the scaffolds, they are originated from the patient's own cell sources that are able to take up normal disc cells' job in synthesizing and regulating new ECM in response to the local milieu so as to maintain the disc structure and function; and growth-stimulating signals, corroborating with the local milieu, which could be biological and physical, to guide the cellular components to perform appropriately.

Seeding cells onto or into pre-cast scaffolds is the approach that dominates the field of tissue engineering. Porous hybrid materials such as bioactive glass and synthetic polymers such as D,L poly(lactide-co-glycolide) (PLGA) have been used as the substrates and surgically inserted into degenerated discs together with cells extracted from the nucleus, as discussed in U.S. Pat. Nos. 5,964,807 and 6,240,926. U.S. Pat. No. 6,723,335 discloses using decellularized IVD nucleus fluid from donor vertebrate for seeding of living cells from the donor, after stabilization using photooxidizing crosslinking. Atelocollagen scaffold has been developed to replace the NP (Sato et al., Med. Biol. Eng. Comput., 41(3):365-71 (2003), Sato, et al., J. Biomed. Mater. Res. A. 64(2):248-56 (2003)). Allograft disc cells demonstrated good scaffold biocompatibility in supporting proliferation and ECM production. The biodegradable synthetic polymer poly-glycolic-acid (PGA) was used to replace the AF and alginate hydrogel to replace the NP after loading with disc cells (Mizuno, et al., Spine, 29(12): 1290-7 (2004)).

The distribution of cells depends on the penetration and migration of the cells into the scaffolds. Unfortunately, penetration of the cells into preformed scaffolds is usually limited to the surface (Seguin, et al., Spine, 29(12): 1299-306 (2004)). The penetration of cells into scaffolds also depends on the pore size of the scaffolds. Large size ensures better penetration but compromises the mechanical properties. Efforts such as agitation during seeding and creating channels in the scaffolds have improved the amount of cells reaching the half thickness of the scaffolds to around 38% (Rose, et al., Biomaterials, 25(24):5507-14 (2004)) but the high speed agitation detrimentally affects cell viability and wide channels detrimentally affect the scaffold properties. Another limitation of the cell-seeding approach is that the distribution of cells in the scaffolds is not homogenous, which may affect the quality of the engineered tissue structures.

Mechanical properties of these scaffolds are not described but the ECM synthesized was far less than required to provide sufficient mechanical support as in the native discs (Masuda, et al., Spine, 29(23):2757-69 (2004)). Taking the mechanical requirement into consideration, there is an attempt to use bone substitute, calcium polyphosphate powder to develop scaffold for NP replacement (Seguin, et al., Spine, 29(12):

1299-306 (2004)). The scaffold allows attachment of disc cells with enhanced proliferation and ECM production but the attachment was only limited to its surface. Further, the compressive modulus of the structures was far less than 100 KPa, only a minor portion of that in the native discs (Urban, et al., *Spine*, 29(23):2700-9 (2004)), reported to range from 3 to 31 MPa in humans (Elliott & Sarver. Spine, 29(7):713-22 (2004)). As a result, the above mentioned approaches may not have sufficient amount of extracellular matrix deposition to provide the necessary mechanical support for intervertebral disc.

Finally, the cell-seeding approach using preformed scaffolds can not be used for production of tissue with heterogeneous structures, consisting of different cell type and intensity, and with different ECM type and intensity, such as invertebral discs. U.S. Pat. No. 6,783,546 discloses a heterogeous structure with a keratin hydrogel sandwiched between layers of synthetic polymers such as silicone and polyethylene for breast reconstruction and NP replacement. However, these synthetic materials have limitations in biocompatibilities. No mechanical properties were reported. The processing of the keratin hydrogel includes heating to temperatures, such as 90° C., which is above the protein denaturation and cell damage so that no living components can be included during the fabrication process. As a result, better fabrication approach for IVD tissue engineering addressing the limitations of the cell-seeding-on-preformed-scaffold approach is warranted.

SUMMARY OF THE INVENTION

A bioengineered IVD for disc replacement as a clinically feasible treatment for patients with severely degenerated IVD has been developed. The disc is built of layers of cells such as MSCs that are encapsulated in a material such as collagen or extracellular matrix. The composition can include factors affecting the differentiation of MSCs such as TGF-beta for chondrocytic lineage. The bioengineered IVD is produced by inducing the self-assembly of a multi-layered structure containing the extracellular matrix and the living cells via MSCs-induced matrix contraction. The MSCs or other living cells can be evenly distributed throughout the bulk of the ECM using this method. The method produces a bioengineered IVD with extra high density collagen as the outermost lamellae of the multi-layered structure with nucleus, inner and outer annulus, strengthened and stabilized by photochemical crosslinking followed by controlled dehydration. The method dehydrates the outermost ECM lamellae in a controlled manner.

A method for expanding MSCs from bone marrow aspirates to sufficient numbers at a controlled rate matching the schedule of "growing" the disc structure and maintaining MSCs in more physiological three dimensional environment in microspheres and with the least extent of in vitro manipulation has also been developed. A means of differentiating mesenchymal stem cells toward chondrogenic-like cells similar to those in intervertebral disc has also been developed.

The method enables the "growth" of IVD-like structures using living cells and natural extracellular matrix in a short period of time, preferably 10 days, so as to minimize the time of in vitro manipulation of the living cells. The methods can produce multiple bioengineered IVDs that can be used for replacement of multiple discs at the same time, or for selection of the structure with the best functional characteristics after in vitro testing using a bioreactor such as that from the commercial source. These methods are capable of producing other multi-layered or heterogeous tissue structures including, but not limited to, G.I. tract and blood vessels. The methods can also be used for cell encapsulation and delivery therapies for disorders such as, cardiovascular, neurological and musculoskeletal systems.

The bioengineered IVD is intact, viable and mechanically comparable to native discs and is ready for implantation as a treatment for severely degenerated IVD that needs replacement. The bioengineered IVD is structurally similar to the native disc with heterogenous structure including a distinct nucleus having collagen and glycosaminoglycans (GAGs) at a ratio similar to that of the native discs, an inner annulus with clear demarcation separating the nucleus and with multiple lamellae of collagen matrix with increasing density and GAGs with decreasing density together with evenly distributed cells of increasing density; and an outer annulus with several lamellae of high density collagen matrix and cells. The collagen-GAGs core can be produced at different ratios and with water content similar to those in native tissues. The method of production also enhances the retention of GAGs in the collagen-GAGs core. The bioengineered IVD has mechanical properties comparable to that of the native disc.

DETAILED DESCRIPTION OF THE INVENTION

Figure 1:
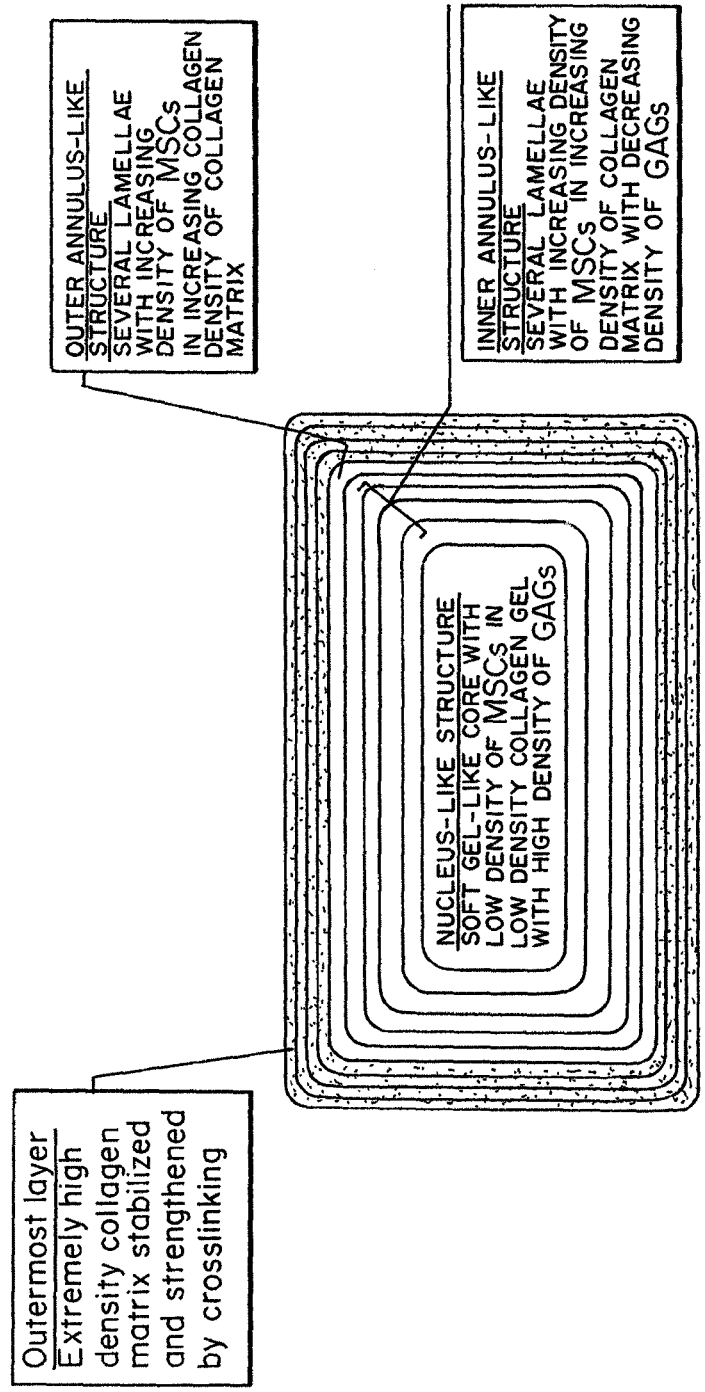
FIG. 1 is a schematic drawing of the bioengineered IVD-like structures.
Figure 2:
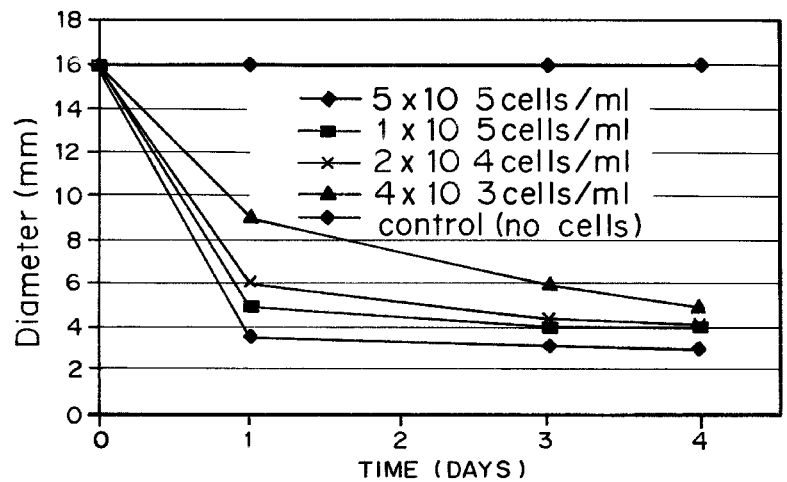
FIG. 2 shows the change in diameter (mm) of MSCs seeded collagen matrix at different cell densities ($5\times10^5$, $1\times10^5$, $2\times10^4$, $4\times10^3$, and control).
Figure 3:
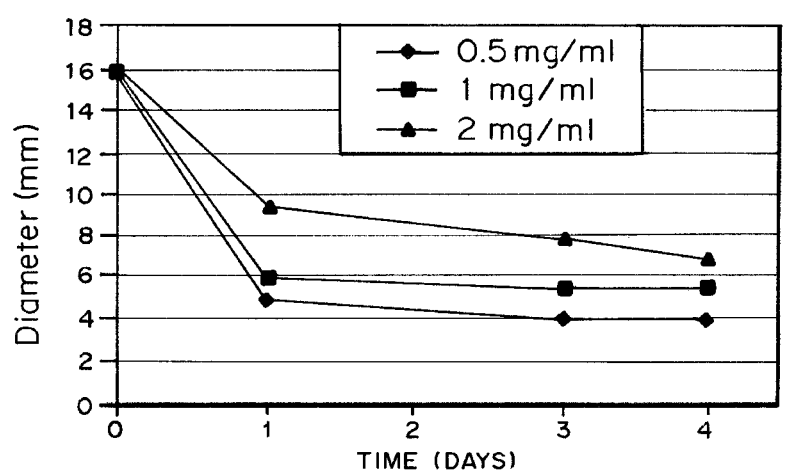
FIG. 3 shows the change in diameter (mm) of MSCs seeded collagen matrix at different collagen matrix densities (0.5 mg/ml, 1 mg/ml and 2 mg/ml over time in days.

A bioengineered IVD for disc replacement comprises an extracellular matrix (ECM) providing support to living cellular components and interacting with the living cellular components during the fabrication process without introducing toxicity. The ECM composition can be from both natural or synthetic sources but preferably natural sources and induced to self-assemble or reconstitute into its solid form under conditions that are mild enough to support cellular survival and growth. The cellular components of the mixture are induced to interact with the matrix in such a way that leads to contraction or shrinkage in volume of the structures, leading to changes in dimension, ECM density, cell density, mechanical property and stability, etc. The extent of the change in volume of the composition can be precisely controlled by factors including, but are not limited to, the density of the ECM, the composition of different ECM, the density of the living cells, the timing for interaction and the serum concentration.

I. Bioengineered Intervertebral Discs

A composition is provided for producing a bioengineered IVD structurally similar to the native disc with heterogeneous structure including a distinct nucleus, an inner annulus and an outer annulus. The composition includes a nucleus consisting of living cells, collagen or other ECM and GAGs at a ratio similar to that of the native discs. The composition can also include an inner annulus with dense ECM lamellae as the clear demarcation separating the nucleus and with multiple lamellae of collagen matrix with increasing density and GAGs with decreasing density (decreasing GAGs:collagen ratio) together with evenly distributed cells with increasing density. Additionally, the composition can include an outer annulus with several lamellae of high density collagen and cells.

A. Components of IVD

The composition consists of collagen and/or other extracellular matrix materials such as proteoglycans/GAGs, elastin, etc., together with mesenchymal stem cells (MSCs) or living cells from human or other clinically feasible sources, and with growth-stimulating signals such as human serum, platelet rich plasma, other blood products, etc. The composition can be induced to self-assemble or "grow" to pre-designed structures before implantation or replacement procedure.

Cells

IVD cells isolated from NP and AF have been used in developing engineered IVD (Mizuno, et al., *Spine*, 29(12): 1290-7 (2004), Seguin, et al., *Spine*, 29(12): 1299-306 (2004)). However, these cells may not be available because they are depleted and non-functional in advanced disc degeneration. Further, sampling autologous disc cells creates donor site morbidities such as degeneration and is thus not preferred. The composition preferably includes mesenchymal stem cells (MSCs) from human or other clinically feasible sources including, but not limited to, autologous, allogeneic, fetal, embryonic or xenogenic sources, either in single cell suspension or encapsulated in matrix microspheres. Adult bone marrow derived MSCs are relatively easy to harvest in large numbers with minimal invasiveness. The MSCs can be derived from autologous bone marrow aspirates, or from matched donor (allogeneic), fetal or embryonic sources, or xenogeneic sources. The isolation of human MSCs (hMSCs) has been described in the literature, for example, U.S. Pat. No. 6,541,024.

Collagen or Other ECM

The ECM providing support to the living cell components can be from either natural or synthetic sources but is preferably natural. The ECM can be induced to self-assemble or reconstitute into its solid form under conditions that are mild enough to support cellular survival and growth. The ECM can interact with the living cells or with other ECM components in such a way that the interaction leads to contraction of the structure and expelling of excessive water. The contraction and the reduction in volume can result in an increase in density of the ECM components and the density of the living cells and hence the mechanical properties. The extent of ECM contraction can be precisely controlled by factors including, but not limited to, the density of the ECM, the density of the living cells, the timing for interaction and the serum concentration.

The ECM can be collagen of various types including but not limited to, type I, II, III, isolated or extracted or prepared from various animal sources including, but not limited to, rat tail, porcine skin, bovine Achilles tendon, and human placenta, in different fractions such as acid-soluble, pepsin-soluble or insoluble. The composition can further comprise other ECM such as proteoglycans/GAGs extracted from cartilage, elastin and hyaluronic acid, or other similar materials. Collagen can be isolated or extracted or prepared from animal sources, such as rat tail, porcine skin, bovine Achilles tendon, or human placenta, and can be from different fractions during collagen extraction, acid-soluble, pepsin-soluble or insoluble, preferably acid-soluble. The collagen used can be those of bovine sources that have been used in FDA-approved skin equivalents Integra® and Apligraf® and can be the soft tissue fillers or products that have been used clinically for wrinkle reduction such as DermaLive and DermaDeep (Bergeret-Galley, et al., *Aesthetic Plast Surg.*, 25(4):249-55 (2001)), or that for urinary incontinence treatment (Corcos, et al., *Urology*, 65(5):898-904 (2005)). Other ECM components such as GAGs extracted from shark cartilage, elastin and hyaluronic acids can be included.

Growth Factors

Additionally or alternatively, the composition can further include growth-stimulating signals such as human serum, platelet rich plasma and other blood products. The composition can further comprise of other factors affecting the differentiation of MSCs such as TGF-beta for chondrogenic lineage. The composition can also contain other factors affecting the differentiation of MSCs such as TGF-beta for chondrogenic lineage.

The composition can also be exposed to growth-stimulating signals other than soluble factors and blood products such as mechanical stimulation simulating that of the forces that an IVD is exposed to prior to the implantation and replacement procedure via bioreactors or equivalent devices. The composition can be induced to "grow" the pre-designed structures before implantation or replacement procedure. The composition can also be exposed to growth-stimulating signals other than soluble factors and blood products such as mechanical stimulation simulating that of the forces that an IVD is exposed to, prior to the implantation and replacement procedure. Autologous serum or plasma, pooled human plasma and platelet-rich-plasma, blood products from matched donor can be included during the fabrication prior to implantation or replacement procedure. Recombinant protein products such as TGF-beta can be included.

Therapeutic, Prophylactic and Diagnostic Agents

The composition can further comprise of other therapeutic, prophylactic or diagnostic agents such as anti-inflammatory drugs and antibiotics.

II. Method of Manufacturing

A method is provided to produce a bioengineered IVD structurally similar to the native disc with heterogeous structure including a distinct nucleus, an inner annulus and an outer annulus. The method produces the nucleus by inducing precipitation of acid soluble collagen and GAGs such as chondroitin-6-sulfate by methods such as stirring, vortexing, centrifugation, shaking, etc at a particular ratio, as demonstrated by the examples. The collagen-GAGs cores are preferably seeded with living cells. The cell density, collagen and GAGs ratios can be predetermined with a certain ratio, as demonstrated by the examples. ECM layers can be laminated by enveloping the previously developed structures by incorporating the previously developed structures into the centre of the reconstituting ECM so that the structures are entrapped and positioned inside the gelling matrix and prior to the formation of the solid phase. The method can be repeated to produce structure of different sizes.

Formation of Collagen or ECM Structure

The IVD structure is fabricated by inducing reconstitution of collagen immediately before the addition of cell suspensions so that the cells are entrapped when the collagen solution transitions to form solid gel. The structure is then made free-floating at a particular time point by removing the attachment of the structure from the surrounding environment. The structures are maintained free-floating until equilibrium of contraction is reached. The extent of contraction, cell and matrix densities and the mechanical properties can be controlled by variables including, but not limited to, the concentration of collagen solution, concentration of MSCs, concentration of GAGs and other ECM, concentration of serum, ratio of collagen to GAGs, duration of incubation.

Preferably the bioengineered IVD is made with a heterogenous structure similar to the native disc, a distinct nucleus consisting of collagen type I and GAGs at a ratio similar to that of the native discs and with a relatively low cell density. In the preferred method, a nucleus like structure is produced using collagen solution at a concentration ranging from 0.25 to 4 mg/ml, preferably 1 mg/ml, neutralized and mixed with glycosaminoglycans (GAGs) such as chondroitin sulfate or dermatan sulfate, from sources such as shark cartilage, at a ratio preferably at around 3:1 (GAGs/Collagen), and MSCs, at an appropriate density ranging from $2\times10^3$ to $1\times10^5$ cells/ml, preferably at $1\times10^4$ cells/ml. The mixture can be cast in a container such as a 4-well culture plate, or a pre-designed container with the shape simulating the IVD, and incubated in a 37° C. incubator for self-assembly or reconstitution for a period of time ranging from 5 minutes to 5 hours, preferably 30 minutes. The structure can be isolated from the surrounding attachment and transferred to a non-adhesive culture plate such as a bacterial culture dish. The structure is incubated to allow for interaction with the living cells for a period of time ranging from 12 hours to 4 days, preferably 1 day, until a pre-designed constant size, preferably the real size of the NP of the mammal such as human, is obtained.

Production of Cells

MSCs from bone marrow aspirates are expanded to sufficient number at a controlled rate matching the schedule of "growing" the disc structure so that the isolated MSCs experience the least amount of in vitro manipulation and are maintained in a more physiological environment. Bone marrow aspirates can be obtained from the patient before a period of time preferably 2 weeks before the implantation procedure. Bone marrow MSCs can be isolated as described in the literature, such as U.S. Pat. No. 6,541,024.

Cells are usually cultured in monolayer and trypsinized upon confluence for subculture in order to have continuous supply of cells. However, as the passage number increases, change in cell morphology and properties can occur. Thus only the first few passages are suggested for use in most cases in stem cell therapy. Nevertheless, the total cell number that can be raised from three passages may still be insufficient and the interval between successive passages is too long for producing multilayered disc-like structures in minimized period of time.

After isolation and cryostorage of the stock. MSCs with a known density are expanded. BM-MSCs can be encapsulated in collagen microcapsules which act as temporary storage for MSCs. Collagen solution is made into appropriate concentrations ranging from 0.1 to 100 mg/ml and preferably used at a concentration of 0.3-4.0 mg/ml, which is neutralized and mixed with MSCs in medium and degassed by methods such as mild centrifugation if necessary. Microcapsules of collagen containing the MSCs are produced using methods including, but not limited to, formation of emulsions with an oil phase, generation of cell-encapsulating collagen droplets using a custom-made droplet generator or a manual or automatic liquid handler or dispenser, and injection of MSCs into preformed collagen microcapsules using microinjector.

The cell-encapsulating microcapsules can be placed into an incubator at 37° C. with 5% $CO_2$ for a period of time ranging from 5 minutes to 10 hours, preferably 30 minutes for reconstitution into collagen gel encapsulating MCSs. MSC encapsulated collagen microspheres were washed in sterile PBS and resuspended in full medium preferably DMEM with HS. The MSC density in collagen solution ranging from $1\times10^3$ cells/ml to $1\times10^7$ cells/ml, and preferably $1\times10^5$ cells/ml. The MSC-encapsulated microspheres are plated onto culture plates at a density between $1\times10^1$ to $1\times10^4/cm^2$, preferably $1\times10^3/cm^2$, in the presence of full medium. The microspheres are incubated at 37° C. for a period of time ranging from 5 minutes to 10 hours, preferably 30 minutes, to allow attachment before filling with full medium. MSCs migrate from the microspheres as early as 1 hour post-plating. When MSCs migrating from the spheres reach a certain density after a period of time ranging from 12 hours to 10 days, preferably 1 day, the microspheres are removed from the culture plates without trypsinization by methods such as gentle flushing with PBS or medium, or picking of the microspheres.

The collected microspheres are sedimented in the incubator for a period of time ranging from 15 minutes to 5 hours, preferably 1 hour, or briefly centrifuged at a speed ranging from 500 to 2000 rpm, preferably 1000 rpm, and replated into new culture plate. The replating procedure can be repeated at a successive interval of a period of time ranging from 12 hours to 5 days, preferably 1 day. MSCs reaching 80-90% confluence can be trypsinized as in monolayer culture for making the IVD structure. As a result, a supply of MSCs from the same passage in the collagen microcapsules, with only one trypsinization, can be obtained at regular intervals, preferably daily, for a period of time ranging from 2 to 30 days, preferably 10 days, that is the period of time necessary for "growing" the IVD structures.

This method allows bone marrow derived MSCs to be expanded to a sufficient number at a controlled rate, with a more physiological environment, and with minimal extent of in vitro manipulation. The method can include microencapsulation of BM-MSCs in three dimensional collagen microspheres using methods including, but not limited to, formation of emulsions, droplets generation and injection of MSCs into preformed collagen microspheres. The method can further include culture and maintenance of the MSC encapsulated collagen microspheres. MSCs outgrowing from the collagen microspheres can be used to produce the IVD structure. The method can further include steps of replating the MSC encapsulated collagen microspheres for multiple times at regular intervals so as to obtain a continuous supply of MSCs without trypsinization. The rate of MSCs outgrowth can be controlled by variables including, but are not limited to the cell density in microspheres, ECM concentration and plating densities of the microspheres.

Addition of Cells to Collagen or ECM

The MSCs or other living cells are evenly distributed throughout the bulk of the ECM irrespective of the dimension and shape of the structures. The method comprises bringing living cells in contact with and mixing them thoroughly with the collagen or ECM solution immediately after reconstitution at low temperature, before the sol-gel transition is completed, to form the solid phase during the fabrication process.

Collagen self-assembly or reconstitution from a solution to a solid gel consisting of fibrils is induced by means including, but not limited to, pH change, preferably an increase from acidic pH to alkaline pH, temperature change, preferably an increase from 4° C. to 37° C., a change in ionic strength by contact with a solution of high ionic strength. The living cells are then brought into contact with the collagen solution mixture containing all necessary growth-stimulation factors and other ECM. Self-assembly or reconstitution of ECM can be speeded up at optimal temperature, preferably at 37° C.

The MSCs or other living cells can be evenly distributed throughout the bulk of the ECM irrespective of the dimension and shape of the structures. For example, the rate of such self-assembly or reconstitution is reduced by maintaining a low temperature, preferably 4° C., during self-assembly or reconstitution so that the MSC or other living cells can be mixed well and thoroughly with the solution collagen containing other soluble growth-stimulation factors and other ECM. The self-assembly or reconstitution rate can be optimized by raising the temperature to 37° C. or by contact with a solution having a high ionic strength such as a PBS concentrate. ECM containing evenly distributed MSCs or other living cells can be obtained after completion of the self-assembly and for a period of time from 5 minutes to 5 hours, and preferably 30 minutes.

The cells embedded in the self-assembled or reconstituted ECM can then be allowed to interact with the ECM, resulting in a change in the properties of the resulting structures, including, but not limited to, the dimension, volume, water content, ECM density, cell density, optical properties, mechanical properties, stability, after isolating the structures from the surrounding environment. The extent of contraction of the ECM can be controlled by adjusting variables, including but not limited to, the concentration of collagen solution, concentration of MSCs, concentration of GAGs and other ECM, concentration of serum, ratio of collagen to GAGs, duration of incubation.

Crosslinking of Collagen or ECM Containing Cells

Retention of GAGs in the core when rehydrating is enhanced by photochemically crosslinking the collagen-GAGs core by first equilibrating with a photosensitizing reagent such as rose Bengal and irradiating with light such as argon laser at 514 nm for a period of time for sufficient crosslinking.

Laminating to Form Multiple Layers

The method of producing a bioengineered IVD with heterogenous structure similar to the native disc, in addition to the nucleus, an inner annulus with clear demarcation separating the nucleus and with multiple lamellae of collagen matrix with increasing density and GAGs with decreasing density together with evenly distributed cells of increasing density can be produced. This method is to laminate dense collagen lamellae onto the nucleus produced by the above mentioned method. The lamellae "enveloping" the nucleus act as the clear demarcation between the nucleus and the annulus and can be produced by first neutralizing collagen solution at a low concentration ranging from 0.25 to 4 mg/ml, preferably at 0.5 mg/ml, second, mixing well with other ECM such as GAGs at a lower ratio preferably at 1.5:1 (i.e., GAGs:collagen ratio approximately 1:5) and with MSCs at a high concentration ranging from $1\times10^4$ to $1\times10^7$ cells/ml, preferably $5\times10^5$ cells/ml, at 4° C. before inducing reconstitution in 37° C. incubator.

After a brief incubation for a period of time ranging from 1 minute to 1 hour, preferably 5 minutes, the nucleus can be transferred into the center of the collagen gel without introduction of any damage or air-bubbles in the same container. The structure can be incubated for a period of time ranging from 15 minutes to 5 hours, preferably 30 minutes, and can be detached from the culture dish. Interaction between the living cells and the ECM can be for a period of time ranging from 12 hours to 4 days, preferably 1 day, until a constant size, ranging from 50 microns to 10 mm preferably 100 microns thicker than the nucleus, can be obtained.

Multiple dense ECM layers enveloping the previously developed nucleus with an increasing collagen density, a decreasing GAGs density and an increasing cell density, at regular intervals, are laminated to form the inner annulus. Multiple dense ECM layers enveloping the previously developed inner annulus with an increasing collagen density and cell density, at regular intervals, can be laminated to form the outer annulus. These methods can be used in custom-made containers of different shapes to produce structures with any shape.

Several denser collagen lamellae, ranging from three to twelve, preferably three, are laminated onto the two-layer structure as the inner annulus. Collagen solution at increasing concentration ranging from 0.25 to 4 mg/ml, and preferably at 0.5, 1 and 2 mg/ml, respectively, are neutralized, mixed with descending GAGs:Col ratio ranging from 1:5 to 1:100, and preferably at 1:9, 1:19 and 1:29, as well as MSCs at increasing concentrations ranging from $1\times10^4$ to $5\times10^9$ cells/, preferably at $5\times10^5$, $1\times10^6$ and $5\times10^6$ cells/ml in medium, respectively. All procedures are conducted in an ice bath before induction for reconstitution in 37° C. incubator. After brief incubation for 5 minutes, the growing structure can be inserted into the center of the newly reconstituted structure and the structure can be allowed to interact with the living cells for a period of time, ranging from 4 hours to 4 days, and preferably 1 day, to a constant size ranging from 50 microns to 10 mm, and preferably 100 microns thicker than the previous structure, before a new cell-matrix layer can be laminated.

In addition to the distinct nucleus and the inner annulus, an outer annulus with several lamellae of high density collagen and cells can be produced. Several, ranging from three to fifteen, and preferably three, very dense collagen lamellae are laminated onto the previous multi-layered structures as the outer annulus. Collagen solution at increasing concentrations ranging from 0.25 to 4 mg/ml, and preferably at 0.5, 1 and 2 mg/ml, respectively are neutralized and mixed with MSCs at increasing concentrations ranging from $1\times10^4$ to $1\times10^7$ cells/ml, and preferably at $5\times10^5$, $1\times10^6$ and $5\times10^6$ cells/ml. All procedures can be conducted in an ice bath before induction for reconstitution in 37° C. incubator.

After a brief incubation for 5 minutes, the growing structure is inserted into the center of the new layer and allowed to interact with the living cells for a period of time ranging from 4 hours to 4 days, preferably 1 day, to a constant size ranging from 50 microns to 10 mm, and preferably 100 microns thicker than the previous structure, before a new layer can be laminated.

Modifying Mechanical Properties of the IVD

The bioengineered IVD is engineered to have mechanical properties comparable to that of the native disc. This can be done by four approaches: (1) by dramatically increasing the density of the ECM lamellae by controlling the extent of contraction after allowing interaction between the living cells and the collagen and other ECM since the mechanical properties increase with the density of the ECM; (2) by dehydrating each individual collagen lamellae so as to increase the ECM density without significant compromise to the cell viability; (3) by enclosing a nucleus structure, which contains the highest water and GAGs content, within the dense ECM envelope or lamellae, which can help in maintaining the hydrostatic pressure of the nucleus; and (4) by a very dense outermost collagen layer strengthened and stabilized by photochemically crosslinking followed by controlled dehydration.

Modifying Density of Disc

The mechanical properties are comparable to that of the native disc, as demonstrated by the examples. The density of the ECM lamellae can be adjusted by adjusting the variables controlling the extent of the ECM contraction, including but are not limited to, cell density, ECM density, duration of interaction between cells and ECM, and serum concentration. The method can also comprise dehydrating each collagen lamellae before formation of successive lamellae without significant compromise in cell viability. Enclosing or enveloping GAGs-containing or retaining nucleus structure with multiple lamellae with low GAGs density, so that the inner structure absorbs more water and thus is more swellable upon rehydration can be used to maintain higher hydrostatic pressure. The IVD structure can also be enveloped with a very dense outermost collagen layer strengthened and stabilized by photochemically crosslinking and controlled dehydration.

Photochemical crosslinking of the outermost collagen layer greatly improves mechanical properties. The high density collagen layer can be laminated onto the previously developed multi-layered structure and the structure brought into contact with a photosensitizing reagent before irradiating with a light source. The photosensitizing reagent employed can be rose Bengal, methylene blue, etc. The light source used can be a laser, a LED, a xenon lamp, etc.

The final structure can be dehydrated by methods including, but not limited to placing against strong water absorbents such as filter paper in a container and gently centrifuging at 500-5000 rpm preferably 1000 rpm for a period of time, ranging from 1 to 100 minutes, preferably 10 minutes to remove excess water. The crosslinked structure is centrifuged in all directions until the outermost layer dehydrates to form a dense layer. In a preferred method of controlled dehydration of the outermost lamellae, the crosslinked structure can be brought in contact with solvents such as ethanol using a method which limits the ethanol to the surface by methods such as spraying until the structure is dehydrated to the appropriate dimension, preferably at 100 microns thicker than the previous multi-layered structure. In a preferred method of controlled dehydration of the outermost lamellae, the structure can be applied with a non-damaging compression force repetitively against water absorbent through the compression platen of a bioreactor from commercial source or a standard weight. The structure can be rehydrated in medium and ready for various tests and implantation. The structure can also be air-dried at a controllable rate by limiting the time of air-drying ranging between 1 hr to 100 hrs, at a time, preferably 5 hrs, and by controlling the number of times of air-drying procedures, ranging from once to 100 times, preferably 3 times, each with substantial rehydration in medium.

The time of manufacture is minimized by minimizing the time for MSC induced collagen matrix contraction for each lamellae using optimized cell and matrix concentration and accelerating the speed of dehydration of the outermost crosslinked lamellae using centrifugation or compression or solvent water extraction.

The methods enable the "growth" of IVD-like structures self-assembled from living cells and natural extracellular matrix in a minimal period of time preferably 10 days so as to minimize the time of in vitro manipulation of the living cells. The time for growing each lamellae of the multi-layered structure can be minimized by methods including but not limited to real time imaging measuring the dimension of the growing structure so that the second lamellae can be induced to "grow" immediately after the dimension of the growing structure has reached plateau. The time for controlled dehydration of the crosslinked lamellae can also be minimized by methods including but are not limited to removing excess water such as centrifugation and solvent water extraction.

The methods also enable the production of multiple bioengineered IVDs that can be used for replacement of multiple discs at the same time, or for selection of the structure with best functional characteristics after in vitro testing using a bioreactor such as that from commercial sources.

The method is also capable of producing other bioengineered tissues with heterogenous structures with multilayer designs including, but not limited to, GI tract such as oesophagus, small intestine, large intestine, and blood vessels, with all possible sizes and shapes, using living cells of different origin and ECM of different types.

III. Bioengineered IVD.

The bioengineered IVD is structurally similar to the native disc with a heterogeous structure including a distinct nucleus consisting of collagen type I and GAGs at a ratio similar to that of the native discs and with a relatively low cell density, an inner annulus with clear demarcation separating the nucleus and with multiple lamellae of collagen matrix with increasing density and GAGs with decreasing density together with evenly distributed cells of increasing density; and an outer annulus with several lamellae of high density collagen and cells, as shown schematically in FIG. 1.

IV. Method of Implantation

The patient having a badly degenerated IVD can be scheduled for IVD replacement after producing the multilayered structure. The structure can be inserted between two vertebrae surgically with posterior ligaments and muscles intact under general anaesthesia. Internal fixation can be used to temporarily provide support and removed after host integration of the implant assessed by radiographic methods.

The present invention will be further understood by reference to the following non-limiting examples.

Example 1

Encapsulation of MSCs in Collagen Microspheres

Materials and Methods

Rattail collagen solution type I was neutralized and diluted into 0.5 mg/ml in the presence of different concentrations ($2 \times 10^4$, $1 \times 10^5$ and $5 \times 10^5$ cells/ml) of human bone marrow derived MSCs in DMEM medium with 10% FBS. The solution was kept at 4° C. in an ice bath before use. A small volume of 5 μl of mixture was dropped onto a non-adhesive substratum using a dispenser. The hMSC containing microdroplets were allowed to reconstitute into microspheres encapsulating the cells by incubating in a 37° C. incubator for 2 hours and were then collected into a DMEM medium containing bath with non-adherent substratum. The collected microcapsules were incubated in 37° C. for three dimensional cultures and the morphological change and the dimensional change of the spheres were recorded for 48 hours before they were ready to be plated onto traditional culture dishes.

Results

Microspheres at day 0 showed individual cells embedding in the collagen matrices and that the microspheres were still transparent. The microspheres contract over time and become more opaque and dense, indicating that cells are reorganizing the matrix to form a tighter matrix containing microspheres.

Example 2

Three Dimensional Culture of MSCs in Collagen Microcapsules, Outgrowth from the Attached Microcapsules and Replating of the Microcapsules

Materials and Methods hMSCs encapsulated collagen microspheres were plated onto 10 mm diameter culture flask at different densities (50, 125 and 250 microspheres per dish) and incubated for 1-2 hours with 1-2 ml of full medium covering the surface of the dish. Afterwards, the dish was gently filled with 8-9 ml more medium. The microspheres were cultured for 3 days and the morphology of the cells migrating out from the microspheres assessed.

Results

Figure 4A:
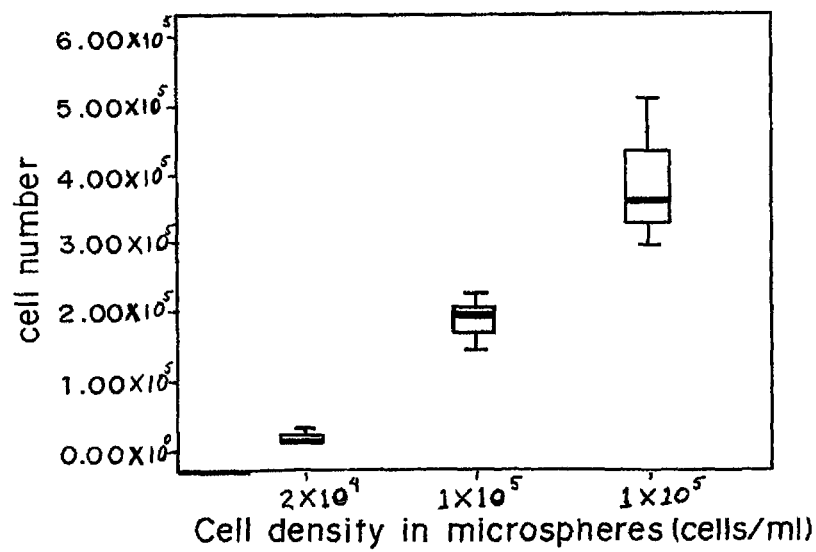
FIGS. 4A and 4B are graphs of the number of hMSCs released from collagen microspheres after 3 days of culture post-platings at different cell density, $2\times10^4$, $1\times10^5$ and $5\times10^5$ (FIG. 4A) and plating density (microspheres/cm$^2$) (FIG. 4B).
Figure 4B:
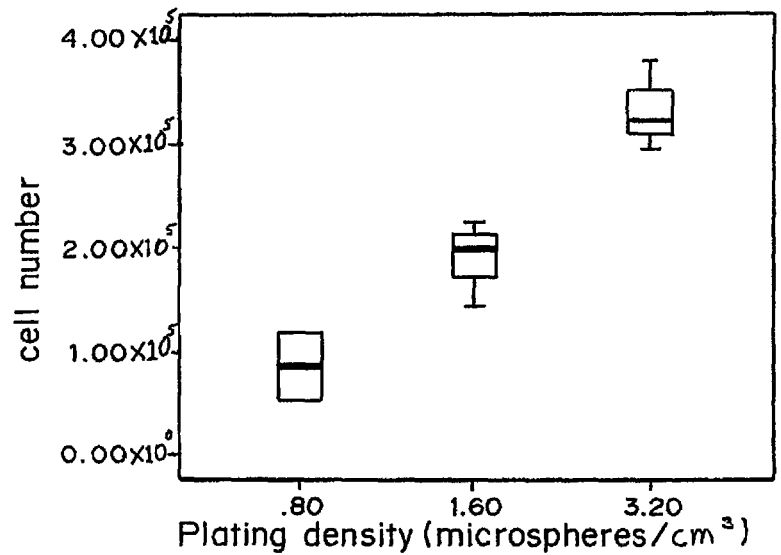

Attachment of the microcapsules onto culture flasks is necessary for cell outgrowth from the microspheres and depends on the cell density and plating density of the cell-encapsulating collagen microspheres on the culture dish. hMSC migrating out from the collagen microspheres showed similar morphology with spindle and elongated shapes. The hMSC-encapsulated collagen microspheres were released from the culture dish by flushing with full medium and replated onto new culture dishes while the cells migrated out from these microspheres were trypsinized for cell count. The growth rate of the hMSCs migrating out from the collagen microspheres was dependent on both the cell density in microspheres and plating density of microspheres in culture dish, as shown by FIGS. 4A and 4B, respectively.

Figure 4C:
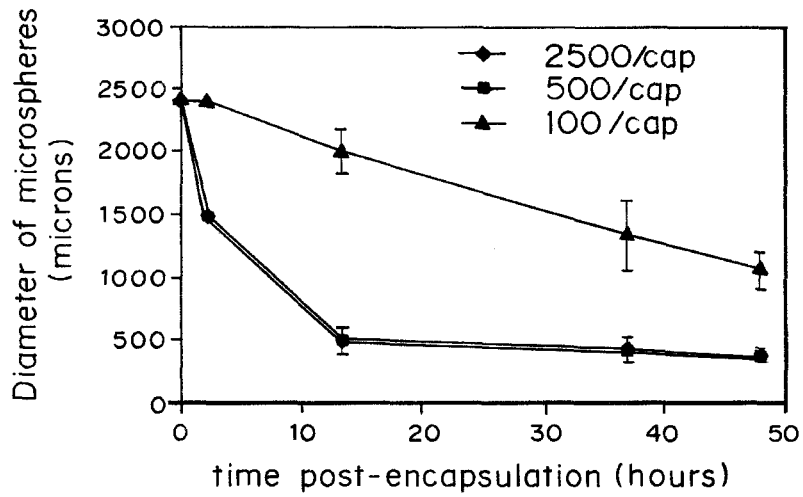
FIG. 4C is a graph of the diameter of microspheres (microns) over time post encapsulation (hours).

MSCs from rabbit bone marrow, when migrating out from the collagen microspheres, were also similar in morphology compared with MSCs in traditional monolayer cultures. rMSCs migrating out from the collagen microcapsules grow at a similar rate with that in monolayer culture and become confluent at a similar period of time, day 4 after plating, as that in the monolayer culture, as shown by FIG. 4C

The migrated MSCs were then trypsinized for subsequent production of IVD structures. The collagen microspheres were reused by first detaching from the culture flasks by gentle flushing with lull medium or by picking. The microcapsules were then sedimented before replating onto a new culture flask for attachment. The replated MSCs migrating out from capsules were similar in morphology and growth rate as compared with that from the monolayer cultures.

Example 3

Production of MSCs Seeded Collagen Matrix, MSCs Induced Collagen Matrix Contraction; Analysis of the Controlling Parameters of the Extent of Contraction

Materials and Methods

Rattail collagen type I solution was neutralized and diluted into concentrations at 0.5, 1 and 2 mg/ml in the presence of rabbit bone marrow derived MSCs at a concentration of $4 \times 10^3$, $2 \times 10^4$, $1 \times 10^5$, $5 \times 10^5$ cells/ml. The collagen MSC mixtures were thoroughly mixed and degassed if necessary and were cast in 4-well plate and incubated for 30 minutes at 37° C. in an incubator. The solidified structure was detached from the culture plate by using a sterile pipette tip or a syringe needle without damaging the structure and was transferred into a non-adherent culture dish such as a bacterial culture dish. The dimension of the structure and the morphology of MSCs inside the structure were recorded against time as the index for volume contraction of the structures.

Results

Contraction of the collagen matrix depends on the presence of living cells. There is no reduction in volume in the absence of the cells. The extent of ECM contraction and reduction in volume depends on the cell density. There was an increasing in the opaqueness of the structure as the cell density increased. The reduction in diameter of the disc structures was measured under a dissection microscope against a micrometer. The extent of matrix contraction is associated with the cell density positively, with an increasing cell density promoting the extent of contraction, and with collagen density inversely, with increasing collagen density reducing the extent of contraction. The reduction in volume was estimated by measuring the diameter of the contracted structure 4 days after incubation and measuring the thickness of the frozen sections of the structures under the microscope. MSCs at different concentrations ($4 \times 10^3$ to $5 \times 10^5$ cells/ml) resulted in volume reduction of collagen matrix ranging from 20 to 75 fold.

Example 4

Fabrication of Multi-Layered Structures with Different Cell and Matrix Density

Materials and Methods

MSCs migrating out from the collagen microcapsules as described in Example 1 and 2 were trypsinzed for production of multi-layered structures. Rattail collagen type I solution was neutralized and diluted to 0.5 mg/ml in the presence of rabbit bone marrow derived MSCs at a concentration of $5 \times 10^4$ cells/ml. The collagen MSCs mixture was cast in 4-well culture plate and induced to self-assemble or reconstitute into solid gel at 37° C. for 30 minutes. The structure was detached from the culture dish and was allowed to interact and contract at 37° C. for 24 hours. A second layer of collagen matrix, after neutralization, at 0.5 mg/ml, was mixed thoroughly with MSCs prepared from the collagen microcapsules at a concentration of $1 \times 10^5$ cells/ml. The structure was incubated at 37° C. briefly for 5 minutes before inserting the contracted structure into the center of the second structure. After incubation for another 30 minutes, the bi-layered structure was again detached from the culture plate and incubated for 24 hours at 37° C. On the following day, a third collagen MSCs structure was produced using 0.5 mg/ml collagen solution and $5 \times 10^5$ cells/ml MSCs prepared as described in Examples 1 and 2. The third structure was induced to reconstitute briefly for 5 minutes at 37° C. before inserting the bi-layered structure into the centre of the third structure. After incubation for 24 hours at 37° C., the dimensions of the three-layered structures were measured and fixed with 4% paraformaldehyde before making 10 microns frozen sections for histological analysis.

Example 5

Fabrication of the Collagen Membrane Strengthened and Stabilized by Photochemical Crosslinking

Materials and Methods

Rattail collagen was reconstituted as described in Example 3 and was equilibrated with excess photosensitizing reagent, rose Bengal at a concentration of 0.01% (w/v) in distilled water, for 2 hours with constant agitation followed by a thorough rinsing with distilled water. An argon laser was used for crosslinking. The laser beam has a spot size of 1.5 cm in diameter covering the whole collagen gel and was delivered in 125 pulses at a power of 0.2 W with pulse duration of 1 s, equivalent to 25 J. Untreated collagen gel was used as the control. Dye control and laser control groups were collagen gels treated with the photosensitizing reagent alone and laser irradiation alone, respectively. Treated collagen gels were air-dried for more than 96 hours to obtain membranes for morphological analysis and measurement of physico-chemical properties. An additional control group of chemically crosslinked collagen produced by treating collagen gel with 0.2% glutaraldehyde solution for 2 hours was used for comparison. Collagen membranes were fully rehydrated in PBS (pH 7.4) at room temperature for more than 24 hours and were carved into a dumbbell shape with a width of 3 mm and a gauge length of 6 mm using a custom-made punch while the gauge length was marked with ink.

The dimensions of collagen samples were measured using a Quick Vision QVPro202 system (Mitutoyo). A tensile testing machine (LR50K, Lloyd Instruments, UK) connected to a load cell of 10N with 0.5% accuracy was used. Fully rehydrated samples were mounted to the custom-made fixtures connecting to the machine. Direct contact between the samples and the fixtures was avoided by placing multiple layers of Kimwipe around the clipping ends of the samples. This prevents slipping and premature failure of the samples during the tensile test. Collagen samples were kept moist by PBS irrigation and excess surface fluid was removed prior to the tensile test. An uniaxial force at a constant strain rate of 5 mm/min was applied to the sample and the force and displacement were recorded at an acquisition rate of 50 data points per second. A CCD camera was used to record the temporal change of the markers at the gauge length of the collagen samples during the tensile test at a rate of 25 frames per second with resolution of 540×720 pixels. The relative displacement between the markers was measured by pixel counting using Photoshop 7.0 for analysis of the strain. Stress-strain curves were obtained and the mechanical properties of the collagen scaffolds, including the peak load, ultimate stress, rupture strain and tangent modulus at 90% of the rupture strain were calculated.

Results

The mechanical properties were enhanced by photochemical crosslinking.

Example 6

Compression Modulus of Multi-Layered Crosslinked Collagen Matrix

Materials and Methods

Crosslinked dry collagen scaffold prepared as described above was rehydrated in PBS (pH7.4) or water for 30 minutes. The rehydrated collagen membrane was rinsed in water or other isotonic solution and the water on the surface of the rehydrated scaffolds removed by blotting dry using kimwipes or other absorbants. The scaffold was carefully laid down at the bottom of a container for reconstitution of collagen gel. The container has a dimension of 15 mm diameter and approximately 7.5 mm thick. 1.5 ml of degassed acid-soluble rattail collagen solution type I at 4 mg/ml was carefully cast onto the collagen membrane. Any air bubbles generated during this process were removed. The membrane-containing collagen solution was then placed in the ammonia chamber for 30 minutes. The procedures were repeated to obtain bi-layered crosslinked collagen membranes. The scaffold was dehydrated by air-drying for more than 24 hours.

Results

By repeating the procedures in Examples 1 and 2, collagen scaffolds appropriate thickness were obtained. For example, 6- or 10-layer collagen scaffold of approximately 1-2 mm thickness produced by the methods described in the examples can be used for intervertebral disc tissue engineering. The multi-lamellae collagen structures made in Example 2 have been fully swollen in phosphate buffered saline at pH 7.4 for 2 weeks. Uncrosslinked structures swell extensively to form a soft gel-like structure with a thickness of around 2 mm. The structures were so weak that they can not be manipulated with forceps and sutures can not be put through. In contrast, crosslinked structures well moderately to a thickness of around 1 mm and were tough. The structures were then mounted on the sample stage of a microforce testing machine fitted with a 100N load cell.

After preloading with a force of around 0.1N, the strain was set to zero and dynamic compression cycles at a frequency of 0.1 Hz and a maximal strain of 0.5 were conducted. The load and unload-diaplacement curves were evaluated while the curve at the 20th cycle was used for data analysis. The compression moduli normalized by the dimension of the samples were obtained.

Results

The stress-strain curves of the uncrosslinked and crosslinked structures were compared. The modulus for the uncrosslinked structures was minimal while the mean value for the crosslinked structure was 4.65 Mpa. The values are comparable with that of rat caudal and lumbar discs, with a mean value of 4.03 and 2.16 Mpa, respectively, and other reported human data ranging from 3-8 MPa. FIG. 13 shows load curve of the twentieth cycle of repetitive compression of photochemically crosslinked collagen layers. FIG. 14 shows the mean compression moduli of photochemically crosslinked collagen layers comparing with that of the lumbar movement segment in human, rabbits, rats and mice native discs.

Example 7

Fabrication and Characterization of the Collagen-GAGs Cores

Materials and Methods

Figure 5:
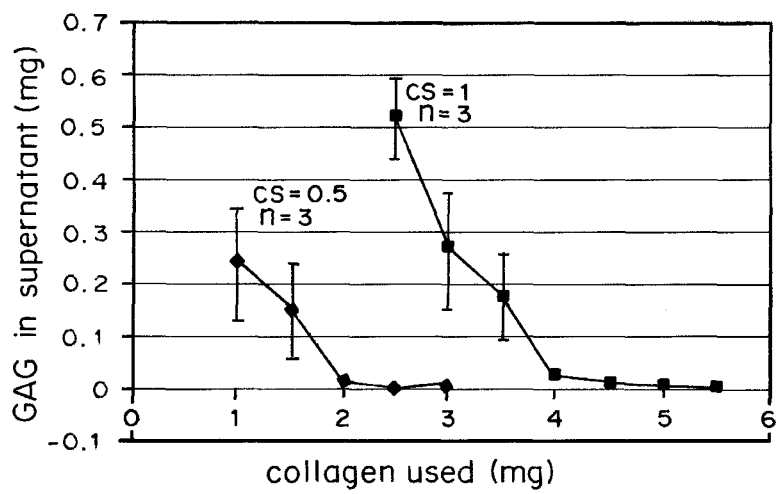
FIG. 5 is a graph showing the mass ratio of collagen and chondroitin 6 sulfate, 0.5 and 1, during precipitation, as a function of GAG in supernatant (mg) versus collagen used (mg).

A collagen and glycosaminoglycans (GAGs) core was fabricated by precipitating an acid soluble solution of collagen with chondroitin-6-sulfate. Precipitation was induced by vortexing the mixture for 1 minute, centrifuging the solid material which were then rinsed with PBS. An optimal mass ratio of collagen to GAGs at 4:1 has been determined, as shown by FIG. 5. The collagen-GAGs core can be photochemically crosslinked as described in Example 5.

Figure 6:
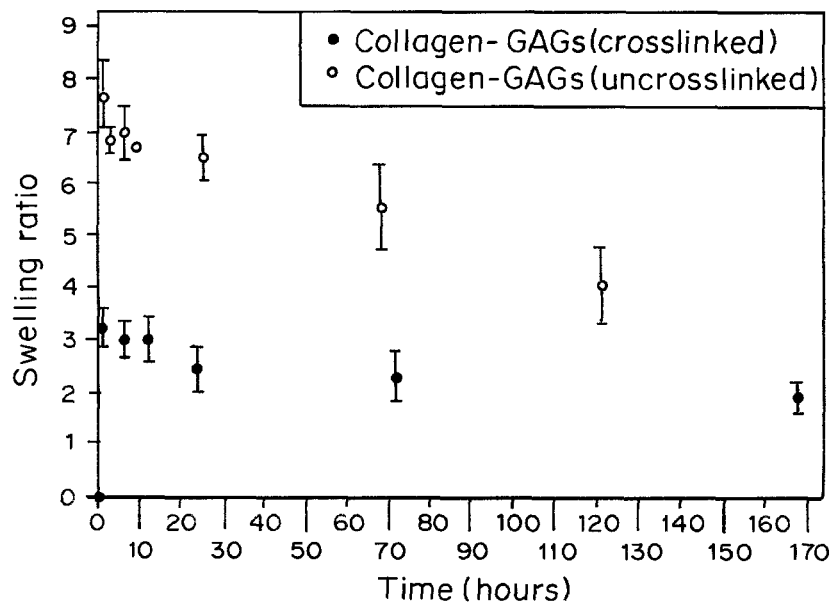
FIG. 6 is a graph of the swelling ratio of collagen-GAGs (chondroitin 6 sulfate) core with and without photochemical crosslinking.

The collagen-GAGs cores were dehydrated, weighted and rehydrated in PBS and the swelling ratio of the cores were calculated by measuring the wet weight at different time points, as shown by FIG. 6.

Results

Figure 7:
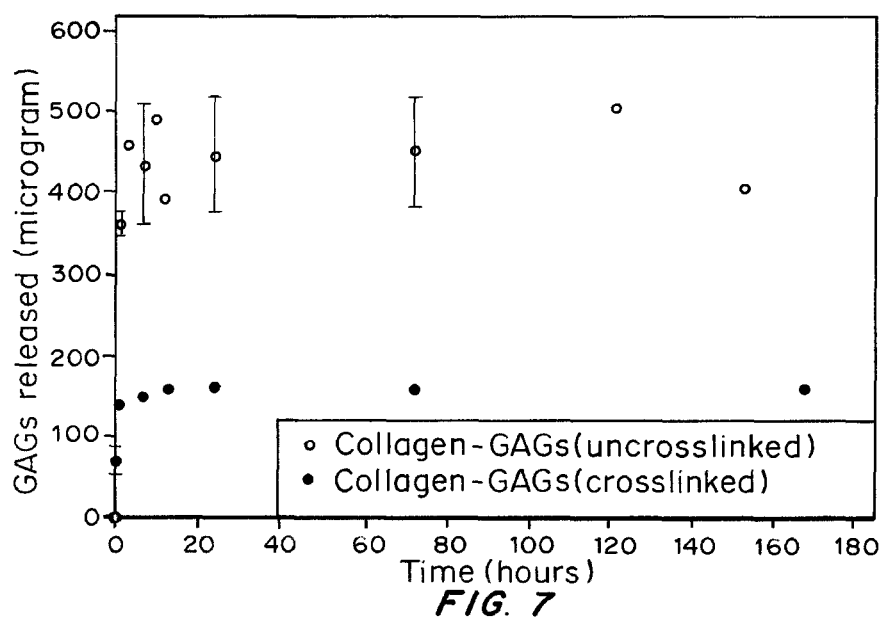
FIG. 7 is a graph showing retention (micrograms released over time in hours) of GAGs in collagen-GAGs core

The uncrosslinked collagen-GAGs rapidly swell to a ratio of 7.5 which is equivalent to a water content of almost 88% while the crosslinked ones swell less rapidly and to a ratio of around 3, equivalent to a water content of around 75%. The high water content is important in creating the swelling pressure when it is inserted into the disc space. The swelling ratio starts to decrease in the collagen-GAGs core as the GAGs content is highly water soluble and the core starts to release GAGs into the surrounding liquid. Photochemical crosslinking is able to retain more GAGs as shown in FIG. 7 as compared to the uncrosslinked ones. This is in agreement with the steady level of the swelling ratio at later time points. The retention of GAGs in the collagen-GAGs core is important in maintaining the structure of the core after implantation. The collagen-GAGs cores are composed of nano-sized fibrils and are porous, thus allowing cell and molecules penetration.

Example 8

Controlled Dehydration of Collagen-Cell Constructs

Methods and Materials

Figure 8:
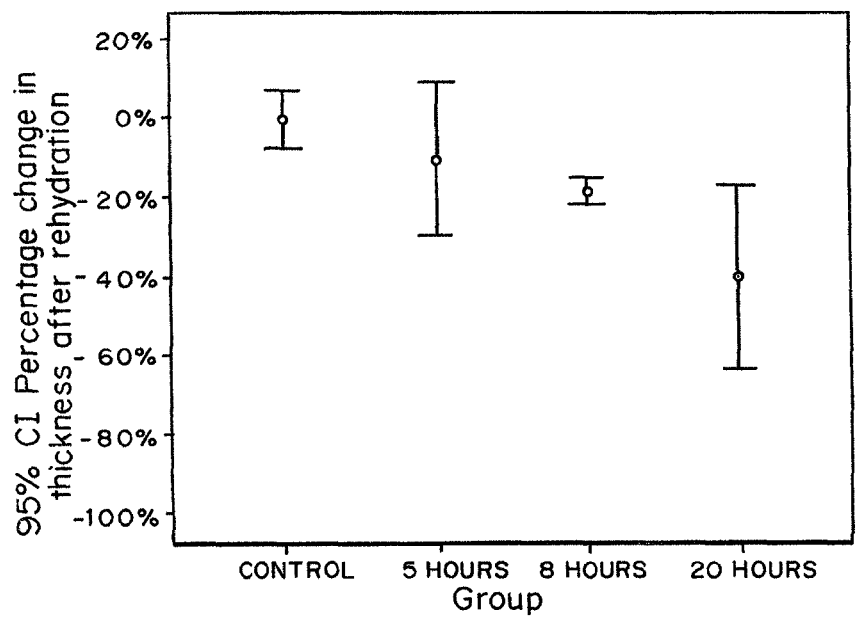
FIG. 8 shows the percent change in thickness of the collagen-cell construct after controlled dehydration for different period of time: control, 6, 8 and 20 hours.

Cell seeded collagen layers were fabricated as described in Example 4 using fibroblasts and collagen type I solution. The collagen-cell constructs were then dehydrated in air in a controlled manner by supplying minimal amount of culture medium to prevent complete dehydration in the incubators. Humid culture chambers were used to maintain a better local humidity. The collagen-cell layers were condensed to a much higher density after the controlled dehydration and the average thickness of the layers reduced after dehydration of different period of time, as shown in FIG. 8. The collagen-cell constructs after dehydration were enzymatically digested to examine cell viability inside the constructs using trypan blue test.

Results

Figure 9:
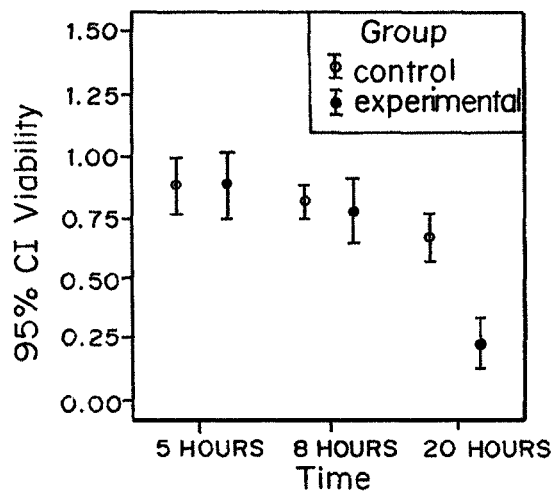
FIG. 9 is a graph showing the percent change in viability of the collagen-cell construct after controlled dehydration for different period of time in hours: 5, 8 and 20 hours.

Controlled dehydration for a continuous period of 8 hours did not differ from that of the controls, which were maintained with a full supply of culture medium while dehydration overnight for 20 hours induced significant higher loss in viability, as shown by FIG. 9. The enzymatically released cells were then replated on culture dishes and the morphology of the cells examined. Those from dehydrated layers are the same as those from the controls, indicating that the cells are still viable and are able to attach and grow normally after dehydration.

Example 9

In Vitro Chondrogenic Differentiation of Human Mesenchymal Stem Cell in Collagen Gel Materials and Methods MSCs were seeded in collagen gel either in the form of microspheres or layers as described in Example 1, 3 and 4. Samples were fabricated with two varying parameters: cell seeding density ($1 \times 10^5$ or $5 \times 10^6$ cells/ml) and collagen concentration (1 or 3 mg/ml). The hMSC-seeded gels were cultured in chondrogenic differentiation medium containing transforming growth factor beta 3 (TGF-β3) for 3 weeks.

Results

Immunohistochemistry showed that collagen type II and aggrecan were synthesized in the gels which were fabricated with high cell seeding density (i.e. $5 \times 10^6$ cells/ml). Sections were strongly stained by Alcian blue staining, indicating a high content of sulfated glycosaminoglycans (GAG). For the samples made with a low cell seeding density (i.e. $1 \times 10^5$ cells/ml) and a low collagen concentration (i.e. 1 mg/ml), cells were found to cluster in the center to produce a localized high cell density region. Collagen type II and aggrecan were detected. However, these gels contained a significantly lower content of GAG, compared to those with high cell seeding density. For the samples made with a low cell seeding density (i.e. $1 \times 10^5$ cells/ml) and a high collagen concentration (i.e. 3 mg/ml), cell clustering was not observed but the cells remain evenly distributed in the matrix. Collagen type II was not detected in these samples and the GAG content was low. These results indicate that hMSCs are able to be differentiate toward the chondrogenic pathway and the cells were chondrocyte-like. These cells also express specific extracellular matrix markers including GAGs, aggrecan and type II collagen, which are expressed in intervertebral disc matrix. The results also indicate that the collagen and cell densities both affect the extent of chondrogenic differentiation.

We claim:

1. An isolated bioengineered intevertebral disc (IVD) for disc replacement, comprising
    an inner annulus and an outer annulus, wherein each annulus is a multi-lamellar structure, the lamellae each comprising cells encapsulated within extracellular matrix (ECM) or collagen,
    wherein the density of the ECM or the collagen of each lamella increases from the inner lamellae to the outer lamellae of each multi-lamellar structure, and the multi-lamellar structure is strengthened and stabilized by crosslinking of the ECM or the collagen, and
    a nucleus core which comprises living cells, collagen and glycosaminoglycans.

2. The bioengineered IVD of claim 1, wherein the cells of the lamellae comprise mesenchymal stem cells (MSC).

3. The bioengineered IVD of claim 2, wherein the MSC are from autologous, allogeneic or xenogenic sources, either in single cell suspension or encapsulated in matrix microspheres.

4. The bioengineered IVD of claim 1, wherein the cells in the lamella are MSC which have been partially differentiated toward a chondrogenic lineage and resemble the chondrocytes in the intervertebral disc.

5. The bioengineered IVD of claim 1, wherein the cells are MSC and the MSC are uniformly distributed throughout the ECM or the collagen.

6. The bioengineered IVD of claim 1, wherein the multi-lamellar structure is formed using collagen solutions at concentrations from 0.2 to 20 mg/ml neutralized and mixed with glycosaminoglycans and MSC at a density ranging from $2 \times 10^3$ to $2 \times 10^7$ mesenchymal stem cells/ml.

7. The bioengineered IVD of claim 1, wherein the ECM comprises collagen of type I, II, or III.

8. The bioengineered IVD of claim 7, wherein the ECM is isolated or extracted from an animal source, wherein the animal source is at least one of rat tails, porcine skin, bovine Achilles tendon, or human placenta.

9. The bioengineered IVD of claim 1, wherein the ECM comprises proteoglycans or glycosaminoglycans extracted from shark cartilage, elastin or hyaluronic acid.

10. The bioengineered IVD of claim 1 wherein the nucleus core comprises the living cells, the collagen and the glycosaminoglycans at ratios to each other similar to the ratio of the living cells, collagen and glycosaminoglycans in the nucleus of naturally occurring IVDs.

11. The bioengineered IVD of claim 1 wherein the inner annulus comprises dense ECM lamellae as the demarcation of the nucleus, the multiple lamellae comprise collagen with increasing density toward the outside of the inner annulus, the multiple lamellae comprise glycosaminoglycans with decreasing density toward the outside of the inner annulus, and the multiple lamellae comprise cells evenly distributed within the lamellae with increasing density towards the outside of the inner annulus.

12. The bioengineered IVD of claim 1 wherein the lamellae of the outer annulus have a higher density of collagen and cells than the lamellae of the inner annulus.

13. A method of making the IVD structure of claim 1, the method comprising encapsulating living cells with a reconstituting ECM or collagen solution to form the inner annulus, the outer annulus and the nucleus core followed by crosslinking the ECM or the collagen containing cells, followed by laminating dense collagen lamellae onto the nucleus, the inner annulus and the outer annulus to form demarcations between the layers.

14. The bioengineered IVD of claim 1, wherein the lamellae of the inner or the outer annulus comprises the collagen lamellae, wherein each of the collagen lamellae is subjected to dehydration before forming successive lamellae.

15. The bioengineered IVD of claim 1, wherein the nucleus has a glycosaminoglycan-nucleus structure that absorbs more water than the lamellae surrounding the nucleus core.

16. The bioengineered IVD of claim 1 further comprising human serum, platelet rich plasma or blood products.

17. The method of claim 13, wherein density of the lamellae during the encapsulation of the cells is increased by adjusting cell density, ECM density, duration of interaction between cells and ECM, or serum concentration.

18. The method of claim 13 wherein the step of encapsulating the living cells comprises evenly distributing the cells throughout the bulk of the ECM or the collagen which are then varied in density from layer to layer of the multi-lamellar or are formed into a density gradient in the inner annulus or the outer annulus.

19. The method of claim 13, wherein change in volume of the lamellae during the encapsulation of the cells is controlled by selection of the concentration of ECM or the collagen solution, concentration of MSCs, concentration of GAGs, concentration of serum, ratio of collagen to GAGs, or duration of incubation.

20. The method of claim 13 further comprising exposing the IVD structure to a mechanical stimulation that the IVD structure is exposed to, prior to an implantation and replacement procedure.

21. The method in claim 13 further comprising, after the outer annulus is formed, bringing the multi-lamellar structure into contact with a photosensitizing reagent and then irradiating with a light source.

\* \* \* \* \*